(12) United States Patent
Besser (10) Patent No.: US 11,389,254 B2
(45) Date of Patent: *Jul. 19, 2022

(54) INSERTION DEVICE POSITIONING GUIDANCE SYSTEM AND METHOD

(71) Applicant: ENVIZION MEDICAL LTD., Tel Aviv (IL)

(72) Inventor: Doron Besser, Tel Aviv (IL)

(73) Assignee: ENVIZION MEDICAL LTD., Tel Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/561,595

(22) Filed: Dec. 23, 2021

(65) Prior Publication Data

US 2022/0117675 A1 Apr. 21, 2022

Related U.S. Application Data

(63) Continuation-in-part of application No. 17/153,060, filed on Jan. 20, 2021, which is a continuation of
(Continued)

(51) Int. Cl.
*A61B 5/00* (2006.01)
*A61B 34/20* (2016.01)
(Continued)

(52) U.S. Cl.
CPC ............ *A61B 34/20* (2016.02); *A61B 5/0033* (2013.01); *A61B 5/0036* (2018.08); *A61B 5/061* (2013.01);
(Continued)

(58) Field of Classification Search
CPC ..... A61B 34/20; A61B 5/0033; A61B 5/0036; A61B 5/061; A61B 5/066; A61B 5/742;
(Continued)

(56) References Cited

U.S. PATENT DOCUMENTS

| 5,558,091 A | 9/1996 | Acker et al. |
| 6,373,240 B1 | 4/2002 | Govari |

(Continued)

FOREIGN PATENT DOCUMENTS

| CN | 102316799 A | 1/2012 |
| CN | 102999902 A | 3/2013 |

(Continued)

*Primary Examiner* — Joel Lamprecht
(74) *Attorney, Agent, or Firm* — The Roy Gross Law Firm, LLC; Roy Gross (57) ABSTRACT

There is provided herein a system and a method for an insertion device positioning guidance system comprising: an electromagnetic field generator configured to generate an electromagnetic field covering a treatment area; a reference sensor configured to be positioned, within the treatment area, on the subject's torso, the reference sensor is configured to define a reference coordinate system representing the position and orientation of the subject's torso relative to the field generator; a registration sensor configured to mark at least a first and a second anatomic locations relative to the reference coordinate system; and a processor configured to operate the field generator, read signals obtained from the reference sensor and the registration sensor, calculate a position and orientation thereof relative to the field generator, generate a 3D anatomic map representing the torso of the subject and the first and second anatomic locations, the processor is further configured to facilitate visualization on the 3D anatomic map of a position, orientation and/or path of a tip sensor, located in a distal tip section of the insertion device, with respect to the first and second anatomic locations, independent of the subject's movement and independent of deviations in the position and/or orientation of the field generator, thus determination of a successful medical procedure is facilitated.

19 Claims, 9 Drawing Sheets

Related U.S. Application Data application No. 15/997,854, filed on Jun. 5, 2018, now Pat. No. 10,898,273, which is a continuation of application No. 15/679,469, filed on Aug. 17, 2017, now Pat. No. 10,010,374.

(60) Provisional application No. 62/376,520, filed on Aug. 18, 2016.

(51) Int. Cl.
  *A61B 5/06* (2006.01)
  *A61B 1/273* (2006.01)
  *A61J 15/00* (2006.01)

(52) U.S. Cl.
  CPC .............. *A61B 5/066* (2013.01); *A61B 5/742* (2013.01); *A61B 5/743* (2013.01); *A61B 1/273* (2013.01); *A61B 5/4233* (2013.01); *A61B 2034/2051* (2016.02); *A61B 2034/2072* (2016.02); *A61B 2034/2074* (2016.02); *A61J 15/00* (2013.01); *A61J 15/0088* (2015.05)

(58) Field of Classification Search
  CPC ....... A61B 5/743; A61B 1/273; A61B 5/4233; A61B 2034/2051; A61B 2034/2072; A61B 2034/2074; A61J 15/00; A61J 15/0088
  See application file for complete search history.

(56) References Cited

U.S. PATENT DOCUMENTS

| | | | |
|---|---|---|---|
| 6,650,927 | B1 | 11/2003 | Keidar |
| 6,690,963 | B2 | 2/2004 | Ben-Haim et al. |
| 7,397,364 | B2 | 7/2008 | Govari |
| 8,046,050 | B2 | 10/2011 | Govari et al. |
| 8,934,960 | B2 | 1/2015 | Besz et al. |
| 10,010,374 | B2 * | 7/2018 | Besser ................ A61B 5/0036 |
| 10,898,273 | B2 * | 1/2021 | Besser ................ A61B 5/0036 |
| 2005/0004456 | A1 | 1/2005 | Thomas et al. |
| 2005/0281385 | A1 | 12/2005 | Johnson et al. |
| 2008/0228066 | A1 | 9/2008 | Waitzman et al. |
| 2009/0234224 | A1 | 9/2009 | Iustin et al. |
| 2010/0097373 | A1 | 4/2010 | Besz et al. |
| 2011/0160569 | A1 | 6/2011 | Cohen et al. |
| 2013/0046172 | A1 | 2/2013 | Waitzman et al. |
| 2014/0243614 | A1 | 8/2014 | Rothberg et al. |
| 2016/0354012 | A1 | 12/2016 | Zeng et al. |
| 2017/0100055 | A1 | 4/2017 | Cronin et al. |
| 2017/0128141 | A1 | 5/2017 | Schneider et al. |
| 2018/0049810 | A1 | 2/2018 | Besser et al. |
| 2018/0368716 | A1 | 12/2018 | Govari et al. |
| 2019/0328620 | A1 | 10/2019 | Cohen et al. |

FOREIGN PATENT DOCUMENTS

| | | |
|---|---|---|
| CN | 107754069 A | 3/2018 |
| CN | 107970074 A | 5/2018 |
| EP | 1374791 A1 | 1/2004 |
| EP | 3284402 A1 | 2/2018 |
| JP | 2001-524012 | 11/2001 |
| JP | 2014-515628 | 7/2014 |
| JP | 2015-502790 A | 1/2015 |
| JP | 2018-27308 | 2/2018 |
| WO | 9849938 | 11/1998 |
| WO | 2007025081 A2 | 1/2007 |
| WO | 2012122002 | 9/2012 |
| WO | 2013078348 | 5/2013 |

* cited by examiner

INSERTION DEVICE POSITIONING GUIDANCE SYSTEM AND METHOD

CROSS REFERENCE TO RELATED APPLICATIONS

This application is a continuation in part of U.S. patent application Ser. No. 17/153,060 filed Jan. 20, 2021, which is a continuation of U.S. Ser. No. 15/997,854 filed Jun. 5, 2018, which is a continuation of U.S. patent application Ser. No. 15/679,469 filed on Aug. 17, 2017, which claims priority to U.S. Provisional Patent Application No. 62/376,520 filed Aug. 18, 2016 which is incorporated by reference as if fully set forth herein in its entirety.

FIELD OF INVENTION

Embodiments of the disclosure relate to insertion device positioning guidance systems and methods.

BACKGROUND

Enteral feeding is often used as nutritional support in patients unable to be fed otherwise. Although many benefits are associated with early initiation of enteral feeding, misplacement of feeding tubes is relatively common and can result in patient discomfort and complications. Confirming the position of the tube only after it is already inserted delays the feeding and the initiating of hydration or medication. Bedside electromagnetic (EM) systems for guided placement of feeding tubes are available and are utilized by medical staff during the procedure to avoid misplacement of feeding tubes. There is still a need, however, for reliable real-time tracking systems that provide enhanced accuracy for critical tool positioning during medical procedures.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods, which are meant to be exemplary and illustrative, not limiting in scope.

One of the problems often associated with an insertion of a feeding tube using an electromagnetic positioning guidance system, is that reliability is difficult to obtain in the patient environment, which is typically dynamic. For example, the patient often moves and the bed is moved from one place to another. There is thus provided herein an electromagnetic positioning guidance system reliably operable regardless of the patient's movement or position and which requires no calibration.

According to some embodiments, there is provided a guidance system for positioning a enteral tube comprising: an electromagnetic field generator configured to be positioned externally to a subject's torso, said electromagnetic field generator configured to generate an electromagnetic field covering a treatment area, an enteral tube comprising a sensor assembly removably positioned within the enteral tube, the sensor assembly comprising an electromagnetic sensor at a distal tip thereof, said electromagnetic sensor configured to sense and/or interfere with the electromagnetic field generated by the field generator, a reference sensor configured to be positioned, within the treatment area, on the subject's torso, the reference sensor is configured to define a reference coordinate system representing the position and orientation of the subject's torso relative to said electromagnetic field, wherein the reference sensor is configured to be positioned independently of the insertion of the enteral tube, a registration sensor configured to mark at least a first anatomic location relative to the reference coordinate system; and a processing circuitry configured to operate said field generator, read signals obtained from the reference sensor and the registration sensor, and calculate a position and orientation of said reference sensor and said registration sensor relative to said electromagnetic field, to generate a 3D anatomic map, representing the torso of the subject and the first anatomic location and a second anatomic location, and to visualize, on the 3D anatomic map, a position, orientation and path of the enteral tube, with respect to the first and second anatomic locations, independent of the subject's movement and independent of deviations in the position and/or orientation of said field generator.

According to some embodiments, the reference sensor is configured to be positioned on a side of the patient's torso, such that the 3D anatomic map further depicts a frontal body contour of the subject and wherein the registration sensor is further configured to mark a second anatomic location on the subject's torso.

According to some embodiments, the reference sensor comprises two reference sensors for positioning below the left and right claviculae respectfully, and wherein a distance between the first and second reference sensors is indicative of the width of the patient's torso. According to some embodiments, the processor is further configured to calculate the position of the second anatomic location (the xiphoid process) based on the position of the two reference sensors.

According to some embodiments, the processor is configured to visualize, on the 3D anatomic map, a position, orientation and path of the sensor or of the sensor assembly positioned within the enteral tube.

In some embodiments, the 3D anatomic map shows a frontal upper view of the subject. In some embodiments, the 3D anatomic map shows a side view of the subject. In some embodiments, the 3D anatomic map shows an axial view of the subject.

In some embodiments, the system further comprises a monitor configured to display the 3D map.

According to some embodiments, the term "anatomic map" as disclosed herein, may refer to one or more schematic maps, one or more 2D anatomic maps, one or more 3D anatomic maps or any combination thereof. According to some embodiments, the term "anatomic map" as disclosed herein, may refer to a group of maps (e.g., 2, 3, 4 or more) maps, each representing a different view (for example, frontal view, frontal upper view, side view, axial view).

In some embodiments, the plate sensor is configured to be positioned under the subject's upper torso and/or neck.

In some embodiments, the registration sensor is a stylus configured to be manually operated.

In some embodiments, the insertion device is a enteral tube. According to some embodiments, the enteral tube is a pediatric enteral tube. According to some embodiments, the enteral tube has outer diameter of 2 mm, 1.5 mm or less or 1 mm or less.

In some embodiments, the first anatomic location is the suprasternal notch and the second anatomic location is the xiphoid process, and wherein a path display of the enteral tube relative to the first and second anatomic locations is indicative of a successful insertion.

In some embodiments, a frontal view display of the path of the enteral tube relative to the first and second anatomic locations is indicative of a successful insertion. In some embodiments, the location where the displayed path (in frontal view) of the enteral tube crosses an axis between the first and second anatomic locations is indicative of a successful insertion. In some embodiments, the actual shape of the displayed path of the enteral tube is indicative of a successful insertion.

According to some embodiments, there is provided a method for guiding an insertion device, the method comprising: utilizing an electromagnetic field generator, applying an electromagnetic field to a treatment area; positioning a reference sensor within the treatment area, on a subject's torso, the reference sensor defines a reference coordinate system representing the position and orientation of the subject's torso relative to the field generator; utilizing a registration sensor, marking at least a first anatomic location; utilizing processing circuitry to operate said field generator, read signals obtained from the reference sensor and the registration sensor, calculating a position and orientation thereof relative to said field generator, generating a 3D anatomic map representing the torso of the subject and the first and second anatomic locations; and displaying on the 3D anatomic map a position, orientation and/or path of a sensor assembly removably positioned within the insertion device, with respect to the first anatomic location and a second anatomic location, independent of the subject's movement and independent of deviations in the position and/or orientation of said field generator.

In some embodiments, the method further comprises displaying a current location, orientation and/or path of the distal tip section of the insertion device on the 3D anatomic map and thus facilitate determination of a successful medical procedure.

In some embodiments, positioning the reference sensor comprises positioning thereof on a side of the patient's torso, such that the 3D anatomic map further depicts a body contour of the subject. In some embodiments, the marking of at least a first and a second anatomic locations comprises utilizing a registration sensor.

In some embodiments, positioning the reference sensor comprises positioning two reference sensors below the left and right claviculae respectively and calculating the position of the second anatomic location based on the width of the subject's torso and the left and right claviculae.

In some embodiments, the method further comprises once a desired position of the insertion device is reached, removing the sensor assembly from the insertion device.

In some embodiments, the method further comprises the step of displaying the path of the distal tip section of the insertion device on the anatomic map and thus facilitates determination of a successful medical procedure. In some embodiments, the distal tip section of the insertion device may include the distal tip section of the sensor assembly, and/or the portion of the sensor assembly which comprises the electromagnetic sensor.

In some embodiments, the 3D anatomic map shows a frontal upper view of the subject. In some embodiments, the 3D anatomic map shows a side view of the subject. In some embodiments, the 3D anatomic map shows an axial view of the subject.

In some embodiments, the registration sensor is a manually operated stylus.

In some embodiments, the insertion device is a enteral tube. According to some embodiments, the enteral tube is a pediatric enteral tube. According to some embodiments, the enteral tube has outer diameter of 2 mm, 1.5 mm or less or 1 mm or less.

In some embodiments, the first anatomic location is the suprasternal notch, and the second anatomic location is the xiphoid process. In some embodiments, a path display of the enteral tube relative to the first and second anatomic locations is indicative of a successful insertion. In some embodiments, the location where the displayed path of the enteral tube crosses an axis between the first and second anatomic locations is indicative of a successful insertion. In some embodiments, the actual shape of the displayed path of the enteral tube is indicative of a successful insertion.

In some embodiments, the electromagnetic field generator is not in any physical contact with the patient. In some embodiments, the electromagnetic field generator is designed not to be in physical contact with the patient. In some embodiments, the electromagnetic field generator is not designed to be in direct or indirect physical contact with the patient.

In some embodiments, the processor/processing circuitry may include two units or two sub-units. The first is configured to control the entire tracking system (e.g., operate the field generator, read signals obtained from the plate sensor, the reference sensor and the registration sensor and calculate a position and orientation thereof relative to said field generator. The second is configured to receive the calculated position and orientation information from the first processor, and use this information to generate a 3D anatomic map representing the torso of the subject and the first and second anatomic locations, and to allow visualization on the 3D anatomic map of a position, orientation and/or path of a tip sensor with respect to the first and second anatomic locations, independent of the subject's movement and independent of deviations in the position and/or orientation of the field generator.

According to some embodiments, the tip sensor, which may also be referred to as a position sensor, is positioned at or adjacent to the distal end of the tube/catheter/stylet and aids in determining the position of the distal end of the tube/catheter/stylet in a patient. According to some embodiments, the tip sensor may include the electromagnetic sensor positioned at the distal end of the sensor assembly. According to some embodiments, the tip sensor may include the electromagnetic sensor positioned at the distal end of the sensor assembly, which may be positioned at the distal end of the insertion device.

The systems and methods described herein may be applied, according to some embodiments, using sensors (e.g., position sensors) such as magnetic field sensors, impedance-based sensors or ultrasonic sensors. According to some embodiments, the position sensor (e.g., tip sensor) may refer to an element mounted on a catheter/tube/stylet, which causes the processing circuitry to receive signals indicative of the coordinates of the element. The position sensor may include a receiver, which generates a position signal to a processing circuitry/control unit based on energy received by the sensor (for example, from the field generator). According to some embodiments, the communication between the sensors and the processing unit may be wireless.

More details and features of the current invention and its embodiments may be found in the description and the attached drawings.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION

Disclosed herein is a system and method for guiding insertion of an insertable medical device (e.g., a tube, such as a feeding tube). The disclosed system may be used as an insertion device positioning guidance system. The system may be used to track and indicate, in real time, the location of an insertion medical device during the insertion process. As one example, the system may track and indicate the location of a tip of a feeding tube as it is being inserted into the body of a subject. Advantageously, this makes the insertion procedure considerably easier and safer, ensuring that the tube is inserted at a correct location.

According to some embodiments, there is provided a guidance system for positioning a pediatric enteral tube, comprising: an electromagnetic field generator configured to be positioned externally to a subject's torso, said electromagnetic field generator configured to generate an electromagnetic field covering a treatment area, an enteral tube comprising a sensor assembly removably positioned within the enteral tube, the sensor assembly comprising an electromagnetic sensor at a distal tip thereof, said electromagnetic sensor configured to sense and/or interfere with the electromagnetic field generated by the field generator, a reference sensor configured to be positioned, within the treatment area, on the subject's torso, the reference sensor configured to define a reference coordinate system representing the position and orientation of the subject's torso relative to said field generator, the reference sensor configured to be positioned independently of the insertion of the enteral tube, a registration sensor configured to mark at least a first anatomic location relative to the reference coordinate system and a processing circuitry configured to: operate said field generator, read signals obtained from said reference sensor and said registration sensor, and calculate a position and orientation of said reference sensor and said registration sensor relative to said electromagnetic field, generate a 3D anatomic map representing the torso of the subject, the anatomic map including the first anatomic location and a second anatomic location, and visualize, on the 3D anatomic map, a position, orientation and/or path of the enteral tube with respect to the first and second anatomic locations, independent of the subject's movement and independent of deviations in the position and/or orientation of said field generator.

According to some embodiments, there is provided an insertion device positioning guidance system comprising: an electromagnetic field generator configured to generate an electromagnetic field covering a treatment area; a plate sensor configured to be positioned within the treatment area in a location defining an orientation of a subject (specifically, the vector perpendicular to the subject's chest); a reference sensor configured to be positioned, within the treatment area, on the subject's torso, the reference sensor is configured to define a reference coordinate system representing the position and orientation of the subject's torso relative to said field generator; a registration sensor configured to mark at least a first and a second anatomic locations relative to the reference coordinate system; and processing circuitry configured to operate said field generator, read signals obtained from said the plate sensor, said reference sensor and said registration sensor, calculate a position and orientation thereof relative to said field generator, generate an anatomic map representing the torso of the subject and the first and second anatomic locations, said processor/processing circuitry is further configured to facilitate visualization on the anatomic map of a position, orientation and path of a tip sensor, located in a distal tip section of the insertion device, with respect to the first and second anatomic locations, independent of the subject's movement and independent of deviations in the position and/or orientation of said field generator, thus determination of a successful medical procedure is facilitated. Optionally, the system further includes a monitor configured to display the map.

A plate sensor is configured to be positioned within the treatment area in a location defining an orientation of a subject (specifically, the vector perpendicular to the subject's chest). The orientation of a subject (specifically, the vector perpendicular to the subject's chest) may be indicated by a plate sensor configured to be positioned within the treatment area. In a non-limiting example, the plate sensor is configured to be positioned under the subject's upper torso and/or neck.

A reference coordinate system representing the position and orientation of the subject's torso relative to the field generator may be indicated by a reference sensor configured to be positioned, within the treatment area, on a subject's torso. The reference sensor may be positioned on a side of the patient's torso, such that the anatomic map further depicts a body contour of the subject.

According to some embodiments, there is provided a feeding tube (or enteral tube) including a feeding lumen for supplying substances to a subject's stomach and/or duodenum, through the esophagus.

According to some embodiments, the system may include a sensor assembly. According to some embodiments, the sensor assembly may be removably positioned within the enteral tube. According to some embodiments, the sensor assembly may include a wire slidably positioned within the enteral tube. According to some embodiments, the sensor assembly may include an electromagnetic sensor. According to some embodiments, the electromagnetic sensor may be positioned at a distal end of the wire, wherein the distal end of the wire may be positioned to correspond with a distal end of the enteral tube. According to some embodiments, the wire may be configured to extend within (or through) the feeding tube (or the enteral tube). According to some embodiments, the wire may be configured to extend within (or through) the feeding tube such that the electromagnetic sensor is positioned at a distal end of the feeding tube. According to some embodiments, the sensor assembly may be slidable within the feeding tube (or the enteral tube). According to some embodiments, the sensor assembly may be less flexible than the feeding tube, thereby guiding the position of the feeding tube within the body of the patient during insertion thereof.

According to some embodiments, the electromagnetic sensor may be a passive electromagnetic sensor, which therefor enables the monitoring of the feeding tube position and/or path, when subject to an electromagnetic field generator (such as, for example, an electromagnetic field generated externally to the patient's body).

Advantageously, since the sensor is passive, (or in other words, does not transmit an electromagnetic field) a field generator external to the patient's body is utilized. Accordingly, a larger electromagnetic field may be generated, which is less sensitive to movements and therefore provides more reliable coordinates of the tube's position. Such coordinates are critical for real-time monitoring of feeding tube positioning including early detection of incorrect insertion into the patient's lungs rather than the stomach.

According to some embodiments, the sensor assembly may be removable from the feeding tube, such that once the feeding tube is positioned within the body of the patient, the sensor assembly may be removed therefrom without shifting the position of the feeding tube.

The electromagnetic sensor may include a sensor body including a core. According to some embodiments, the core may be coupled to the wire configured to extend along the length of the feeding tube. According to some embodiments, the electromagnetic core may be positioned at a distal end of the sensor assembly.

According to some embodiments, the sensor assembly may include a printed circuit board (PCB). According to some embodiments, the electromagnetic sensor may be coupled to the printed circuit board. According to some embodiments, the core and the wire may be directly or indirectly attached to the PCB. According to some embodiments, the PCB may be a FR-4 PCB.

According to some embodiments, the core may include a coil, such as a coil made of one or more copper wires wound around at least part of the core, also referred to herein as a "core assembly". According to some embodiments, the one or more copper wires may have a diameter of between 10 μm and 70 μm. According to some embodiments, the one or more copper wires may wound around the core between 40 and 3000 turns of wire around the core. According to some embodiments, the sensor body may have an outer diameter of 1 mm or less, such as but not limited to an outer diameter of 0.8 mm.

According to some embodiments, the wire running along the sensor lumen may be a twisted wire, such as but not limited to a wire made of two intercalated and/or braided wires. According to some embodiments, the wire may be a pair of twisted copper wires. According to some embodiments, the wire may have an outer diameter of 0.5 mm or less, or 0.4 mm or less, such as but not limited to an outer diameter of 0.35 mm.

The first and the second anatomic locations may be indicated by a registration sensor configured to mark at least the first and the second anatomic locations relative to the reference coordinate system. Optionally, the registration sensor is a stylus configured to be manually operated. Optionally, the first anatomic location is the suprasternal notch and the second anatomic location is the xiphoid process, and a path display of the enteral tube relative to the first and second anatomic locations is indicative of a successful insertion.

The electromagnetic field generator may be static throughout a duration of a procedure for placing a tube within a body of a subject. In such cases, a region covered by the electromagnetic field is static/constant throughout the duration of a procedure for placing a tube within a body of a subject. Advantageously, the static electromagnetic field may contribute to the accuracy of the display.

The anatomic map may show a frontal upper view of the subject essentially parallel to the plate sensor and/or a side view of the subject essentially perpendicular to the plate sensor and/or an axial view of the subject.

One example of hardware suitable for use as the above-mentioned electromagnetic tracking system, including the electromagnetic field generator and one or more of the sensors, is the Aurora® system by Northern Digital Inc., of Ontario, Canada.

Throughout the following description, similar elements of different embodiments of the device are referenced by element numbers differing by integer multiples of 100. For example, an electromagnetic field generator of FIG. 1 is referenced by the number 102, and an electromagnetic field generator of FIG. 2, which corresponds to electromagnetic field generator 102 of FIG. 1, is referenced by the number 202.

Figure 1:
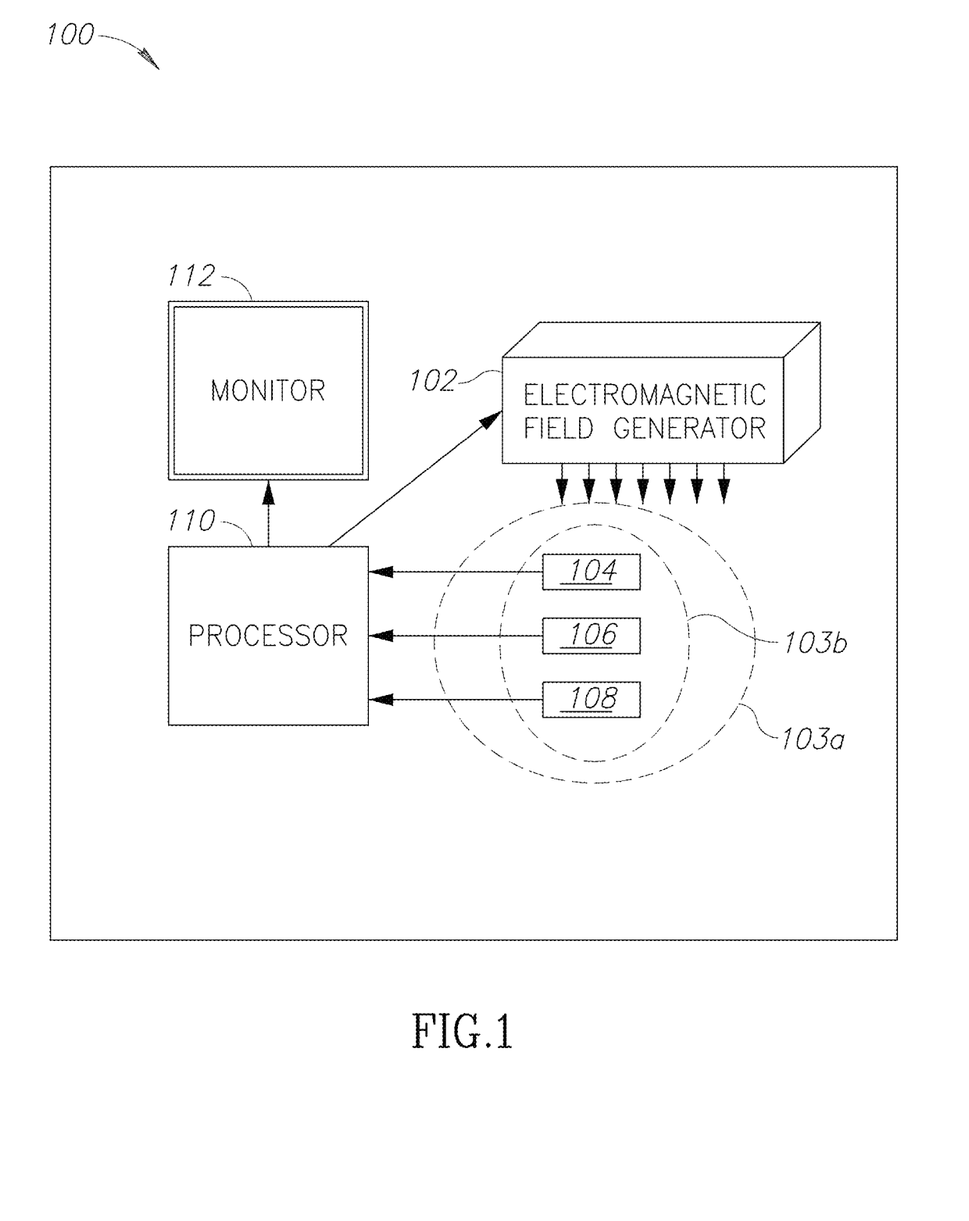
FIG. 1 is a block diagram of an insertion device positioning guidance system, in accordance with some embodiments.
Figure 2A:
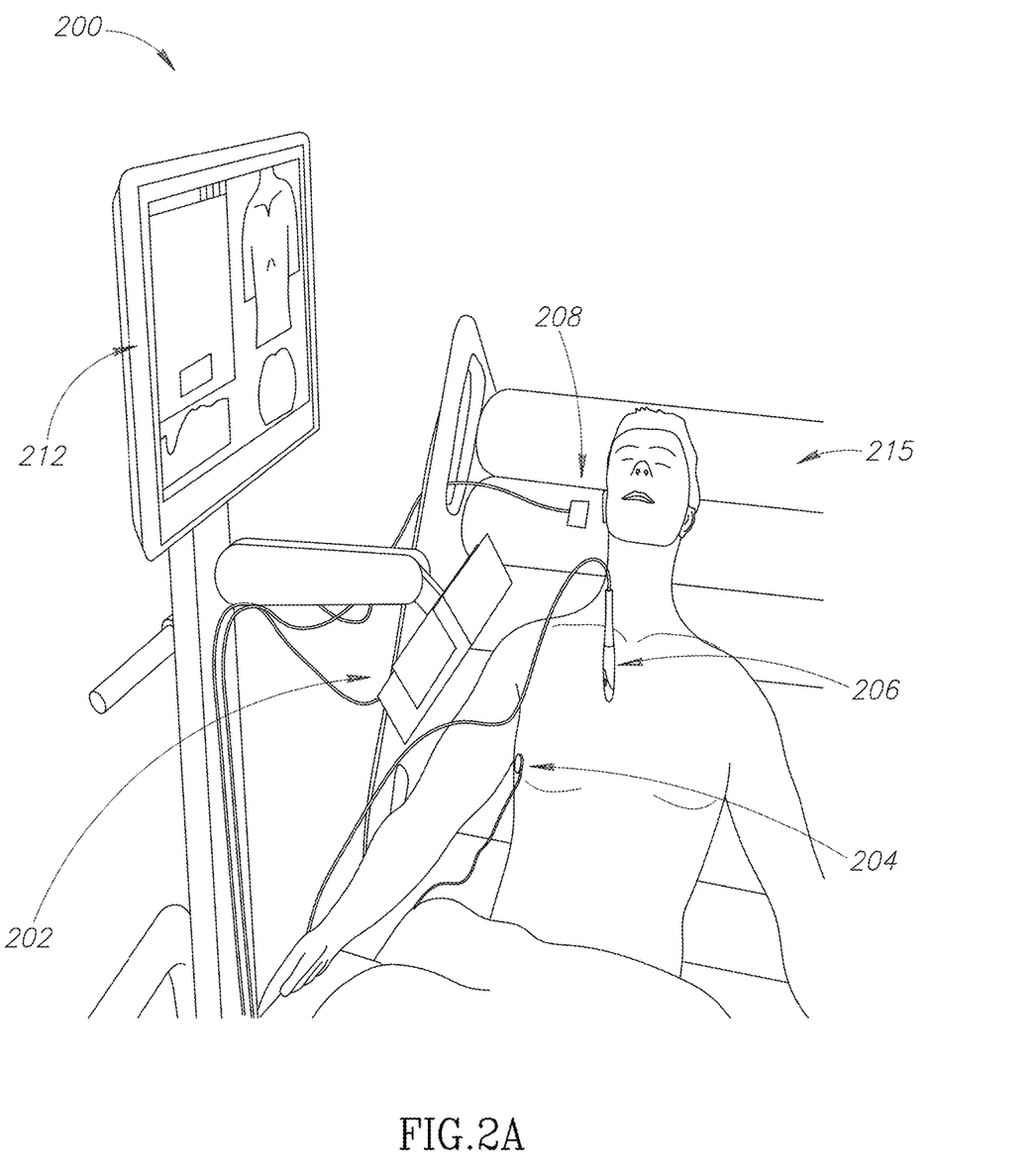
FIG. 2A schematically illustrates an insertion device positioning guidance system in a hospital setting, in accordance with some embodiments.

Reference is now made to FIG. 1 which is a block diagram of an insertion device positioning guidance system 100. System 100 includes an electromagnetic field generator 102 configured to generate an electromagnetic field 103a covering at least a region of interest 103b (e.g., a treatment area such as a patient's torso), a plurality of electromagnetic sensors, such as sensors 104, 106, and 108, to indicate a position of a tip sensor (located in a distal tip section of the insertion device) on an anatomical map (FIGS. 3A-B) of the region of interest 103b (typically the subject's torso). System 100 further includes a processor 110 configured to operate said field generator, read signals obtained from the plate sensor, the reference sensor and the registration sensor, calculate a position and orientation thereof relative to said field generator, and generate the anatomic map representing the torso of the subject. Processor 110 is configured to facilitate visualization on the anatomic map of the position and path of the tip sensor, with respect to predesignated anatomic locations, independent of the subject's movement and independent of deviations in the position and/or orientation of field generator 102. System 100 further includes a monitor 112 operatively connected to processor 110 and configured to display, on the anatomic map, the positions of and/or the path leading from the insertion device tip to the insertion site. In some embodiments, monitor 112 may be integrated with processor 110, such as in the case of an all-in-one computer. A determination of a successful medical procedure (for example, an insertion of a feeding tube to the stomach as opposed to the lungs) is thus possible.

Sensor 108 is typically a plate sensor configured to be positioned within the treatment area in a location defining an orientation of a subject. Optionally, the location is indicative of a subject's posture. Plate sensor 108 is optionally a 6-DOF (Degreed-of-Freedom) electromagnetic sensor. Plate sensor 108 is optionally positioned in the bed of the subject and is configured to mark the posture of the subject by marking the positon of the bed. Alternatively, plate sensor 108 may be attached to the subject's body. Optionally, plate sensor 108 is positioned under the subject's back. Optionally, plate sensor 108 is positioned under the subject's upper torso and/or neck. In case plate sensor 108 is kept adjacent to the subject's back, it may indicate if the subject is lying, lying with his upper body partially lifted or sitting. Reference sensor 108 may be, for example, a 6-DOF electromagnetic sensor, capable of determining 6 axes of its location (XYZ axes) and attitude (roll, yaw, and pitch) with respect to field generator 102.

Sensor 104 is typically a reference sensor configured to be positioned on a subject's torso. Reference sensor 104 is configured to define a reference coordinate system representing the position and orientation of the subject's torso relative to the field generator. Optionally, reference sensor 104 may be attached to the skin of the patient, for example on the side of a patient's torso such as beneath the patient's armpit. In such cases, the anatomic map further depicts a body contour of the subject. Reference sensor 104 may be, for example, a 6-DOF electromagnetic sensor, capable of determining 6 axes of its location (XYZ axes) and attitude (roll, yaw, and pitch) with respect to field generator 102.

Sensor 106 is typically a registration sensor configured to be positioned on and/or to mark at least a first and a second anatomic (thoracic) locations over the subject's body (e.g. the subject's torso). Different anatomical locations may be marked depending on the type of procedure used, the type of insertion medical device, etc. The marking of the anatomic location may be physical, such as attaching a marker/fiducial (such as a sticker). Alternatively, the marking of the anatomic location may be virtual, such as registering a virtual marker/fiducial. The marking, in accordance with embodiments, may facilitate identification or designation of an anatomical location within or on a subject's body such as, in a non-limiting example, a subject's suprasternal notch, and a subject's xiphoid process.

Optionally, registration sensor 106 is a stylus sensor configured to be manually operated to mark at least a first and a second anatomic location over the subject's body identified by the operator of the stylus. The marking may be made, merely as an example, by indicating to the software (for example, but not limited to, by pressing a GUI button or voice activation) once stylus sensor 106 is positioned over the desired point on the patient's body. The marking may be communicated to and/or registered by processor 110.

System 100 is configured to work in conjunction with an insertion medical device (not shown), such as a feeding tube. The insertion medical device may include one or more sensors to allow its tracking within region of interest 103b. Preferably, the sensor is located at the tip of the insertion medical device. In such case, processor 110 and monitor 112 are configured to compute and display position and/or advancement of the tip of the insertion medical device between the designated anatomical locations leading to the insertion site/target area.

According to some embodiments, as used herein the terms "insertion device" and "insertion medical device" may refer to any device/tool adapted for insertion into a body. The insertion device may be any medical insertion device or a medical surgical device. Non-limiting examples of insertion medical devices include, feeding tubes, such as enteral tubes (for example, nasoenteral feeding tubes), endotracheal tube, tracheostomy tube, stomach tube, catheter tubes or cricothyrotomy tube. Other examples of insertion devices are well known in the art.

According to some embodiments, the terms "processing circuitry" and "processor" may be used interchangeably.

In some embodiments, the insertion device is a tube. In some embodiments, the tube is a feeding tube. In some embodiments, the tube is an enteral feeding tube, such as, but not limited to, a nasogastric feeding tube or a nasoenteral feeding tube. According to some embodiments, the feeding tube may have disposed therein and/or thereon an electromagnetic sensor, for example at its distal end. According to some embodiments, the enteral tube is a pediatric enteral tube. According to some embodiments, the insertion device is a naso-gastric pediatric feeding tube.

Figure 2B:
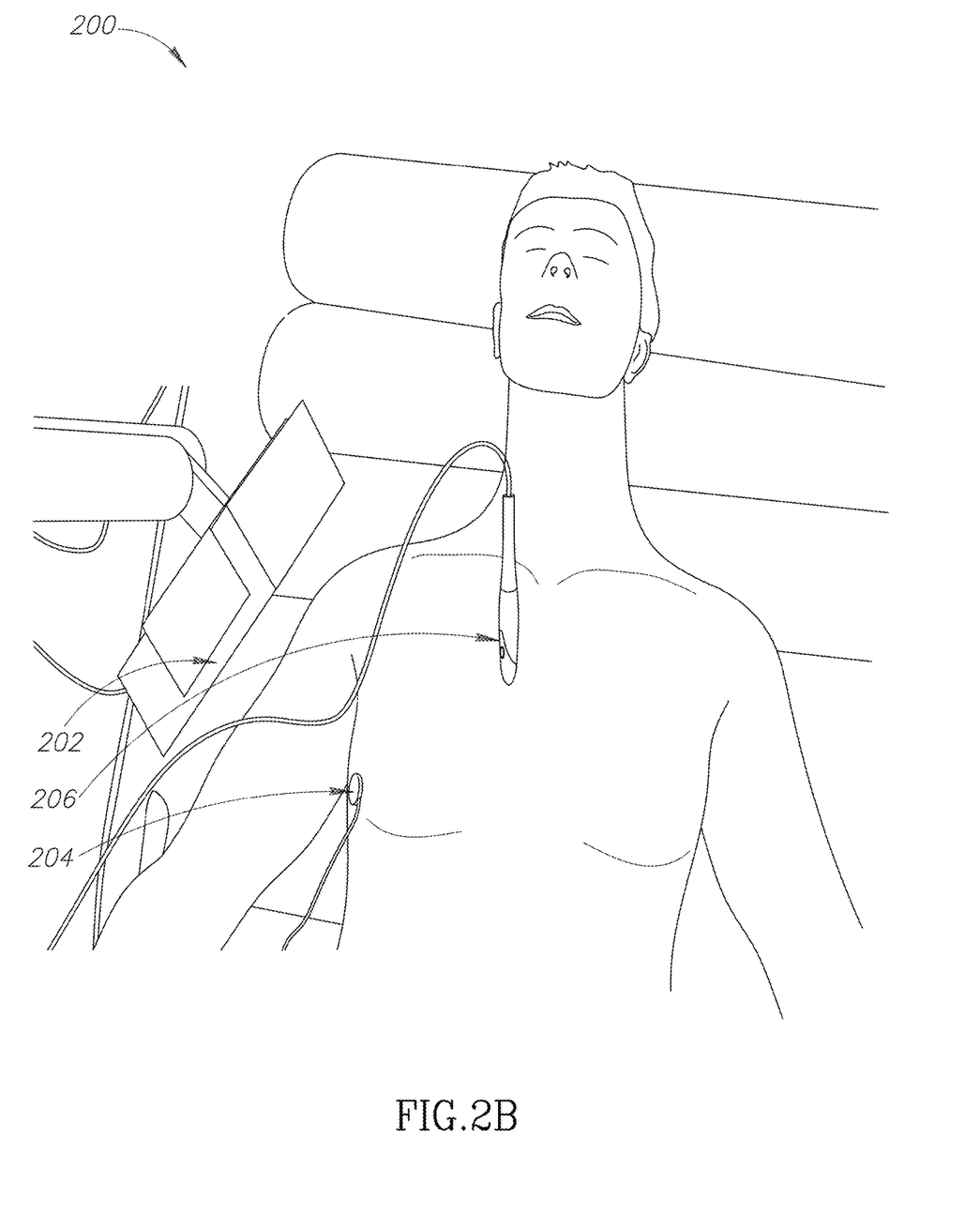
FIG. 2B shows an enlarged portion of the illustration of FIG. 2A, in accordance with some embodiments.
Figure 2C:
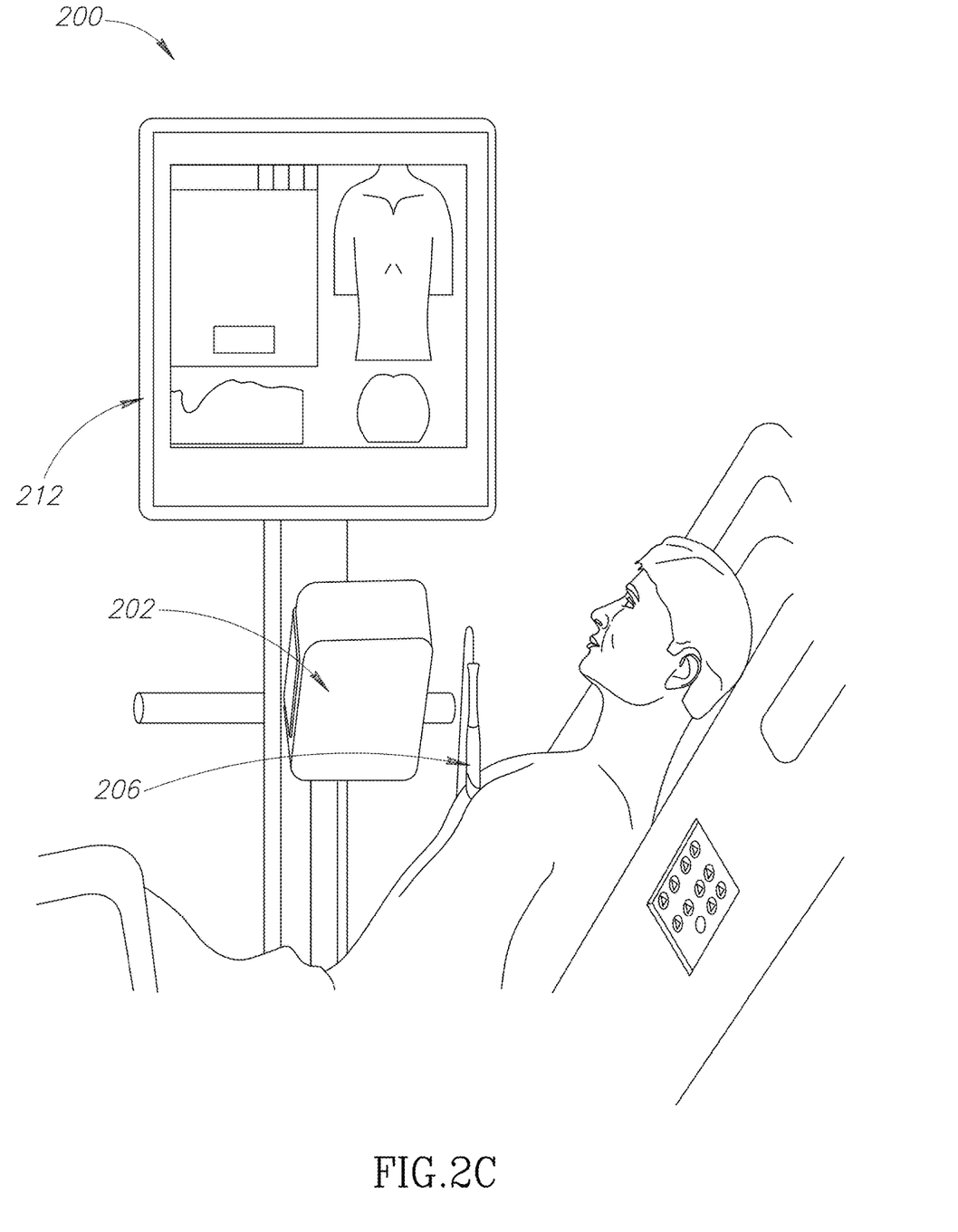
FIG. 2C shows a side view of the illustration of FIG. 2A, in accordance with some embodiments.
Figure 2D:
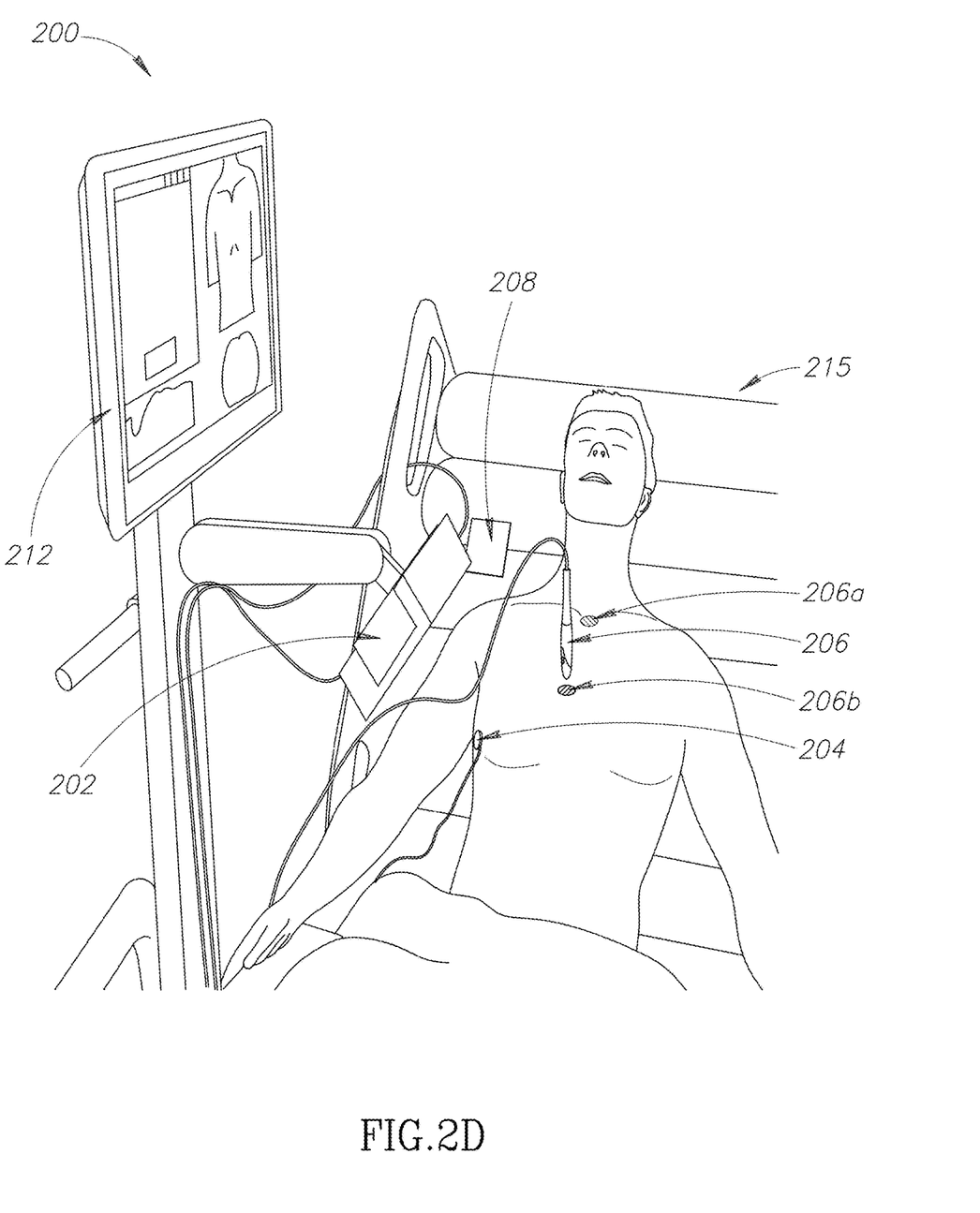
FIGS. 2D-E schematically illustrate an insertion device positioning guidance system in a hospital setting, showing anatomic locations marked using a stylus, reference sensor and plate sensor located at different locations, in accordance with some embodiments.
Figure 2E:
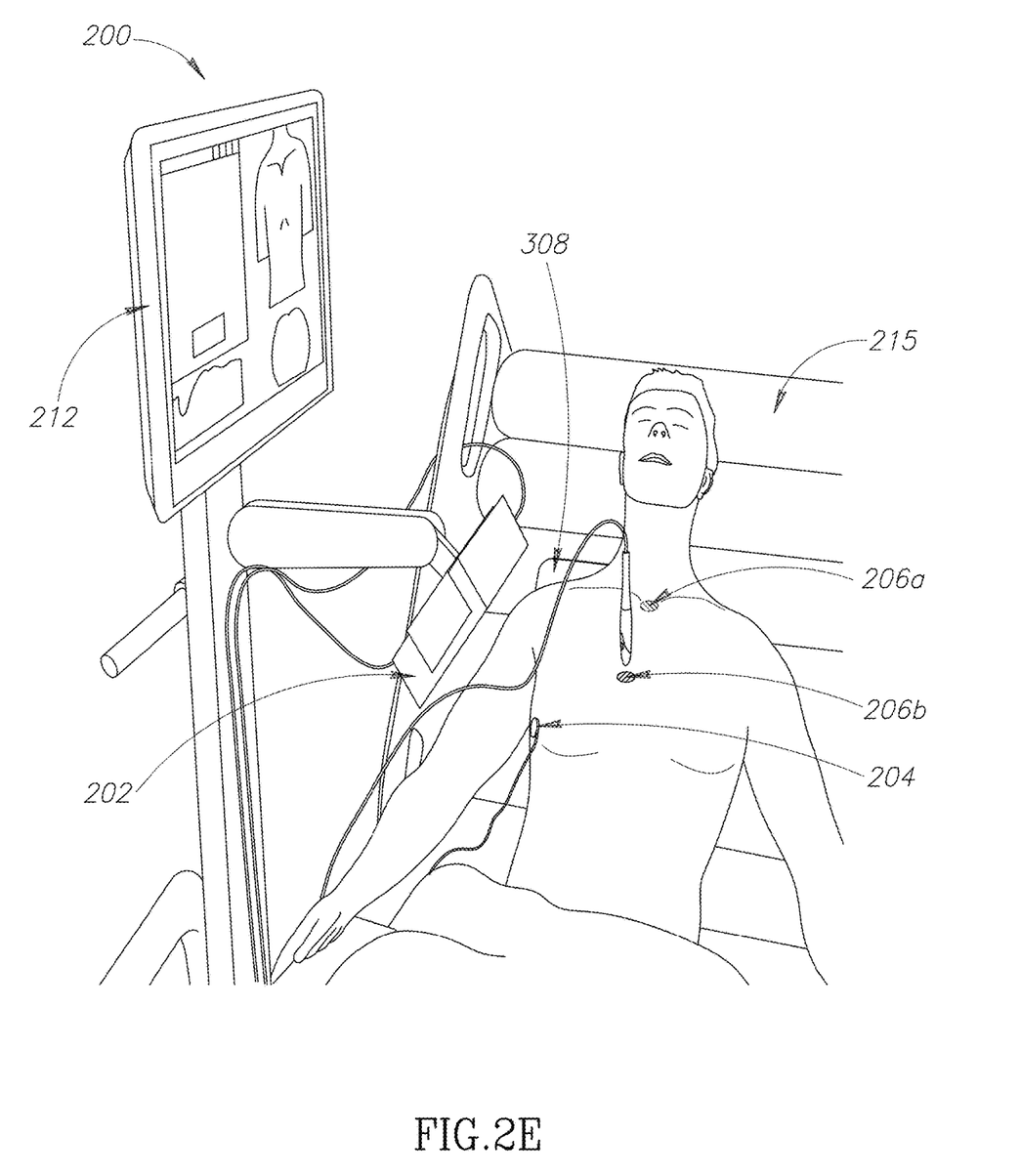

Reference is now made to FIGS. 2A-E which schematically illustrate an insertion device positioning guidance system 200 in a hospital setting, in accordance with some embodiments. FIG. 2A schematically illustrates an insertion device positioning guidance system in a hospital setting, in accordance with some embodiments, FIG. 2B shows an enlarged portion of the illustration of FIG. 2A, in accordance with some embodiments, FIG. 2C shows a side view of the illustration of FIG. 2A, in accordance with some embodiments and FIGS. 2D-E schematically illustrate an insertion device positioning guidance system in a hospital setting, showing anatomic locations marked using a stylus, reference sensor (as shown in FIGS. 2A-C) and plate sensor located at different locations, in accordance with some embodiments.

Similarly to system 100 of FIG. 1, system 200 includes an electromagnetic field generator 202, and a plurality of electromagnetic sensors 204, 206, and/or 208. Further, system 200 is configured to work in conjunction with an insertion medical device (not shown) which may include one or more electromagnetic sensors configured to sense and/or interfere with the electromagnetic field generated by field generator 202. Optionally, monitor 212 of system 200 is integrated with a computer, which corresponds to or includes processor 110 of FIG. 1.

According to some embodiments, electromagnetic field generator 202 may be positioned at such angle and position with respect to the patient, as to enable the generated electromagnetic field to cover the external and internal working area, or in other words, the entire upper torso (at least from the nose area to the duodenum area). Reference sensor 204, plate sensor 208, and stylus sensor 206 are all covered under the field produced by field generator 202. The tip sensor of the feeding tube is configured to move inside the digestive system, and its path can thus be traced. Reference sensor 204 may be attached to and/or on the skin of the patient, for example beneath the patient's armpit. Suitable means for attachment of the sensor are well known in the art such as, for example, stickers, medical glue and the like. Reference sensor 204 may serve to detect location (XYZ axes) and attitude (roll, yaw, and pitch) of the patient with respect to field generator 202, based on the electromagnetic field (not shown) emitted by field generator 202.

As discussed herein, plate sensor 208 may be positioned at a location which defines an orientation of a subject (or at least the orientation of the body part that is being treated).

For example, if the medical insertion procedure involves the patient's torso, plate sensor 208 may be positioned on the part of the patient's bed 215 parallel to the torso, as shown in FIG. 2D. Alternatively, as shown in FIG. 2E, a plate sensor 308 is inserted at least partially between the patient's back and bed 215.

Stylus sensor 206 may be manually operated to mark one or more anatomic locations over the patient's skin. For example, FIGS. 2D and 2E show the marking of two such anatomic locations (indicated as "206a" and "206b" in these figures) on the patient's chest. Anatomic location 206a is marked over the suprasternal notch, and anatomic location 206b is marked over the xiphoid process. The marking may be communicated to and registered by the computer.

Optionally, the computer receives signals of the locations and postures of reference sensor 204, plate sensor 208, and the two marked anatomic locations 206a and 206b, and computes an anatomic mark representative of the subject's torso, thereafter the medical procedure can begin. In the exemplary case of guiding the insertion of a feeding tube, the tip of the feeding tube is equipped with a sensor. Optionally, the computer receives the actual position and orientation of the sensors from a second processor that receives the signals and calculates the sensors' locations. Optionally, the computer receives the actual position and orientation from a second processor that receives the signals from the sensors and calculates their physical location.

System 200 is operated as follows:

The electromagnetic field generator 202 is activated to apply an electromagnetic field to the treatment area, covering the subject's torso;

Plate sensor 208/308 is positioned within the treatment area in a location defining an orientation of a subject (or at least the orientation of the body part that is being treated), for example, on the bed beneath the subject's torso;

Reference sensor 204 is positioned within the treatment area, on a subject's torso, preferably on the side of the torso. Reference sensor 204 defines a reference coordinate system representing the position and orientation of the subject's torso relative to the field generator;

Registration sensor 206 is used to mark two anatomic locations on the subject's torso (for example, the suprasternal notch and the xiphoid process);

Utilizing a processor, generating an anatomic map representing the torso and the two anatomic locations and displaying on monitor 212 the anatomic map and the position and path of the tip sensor (of the feeding tube). The path of the tip sensor may be displayed with respect to the two anatomic locations and/or with respect to a longitudinal axis passing between the two anatomic locations and along the center of the torso.

Figure 3A:
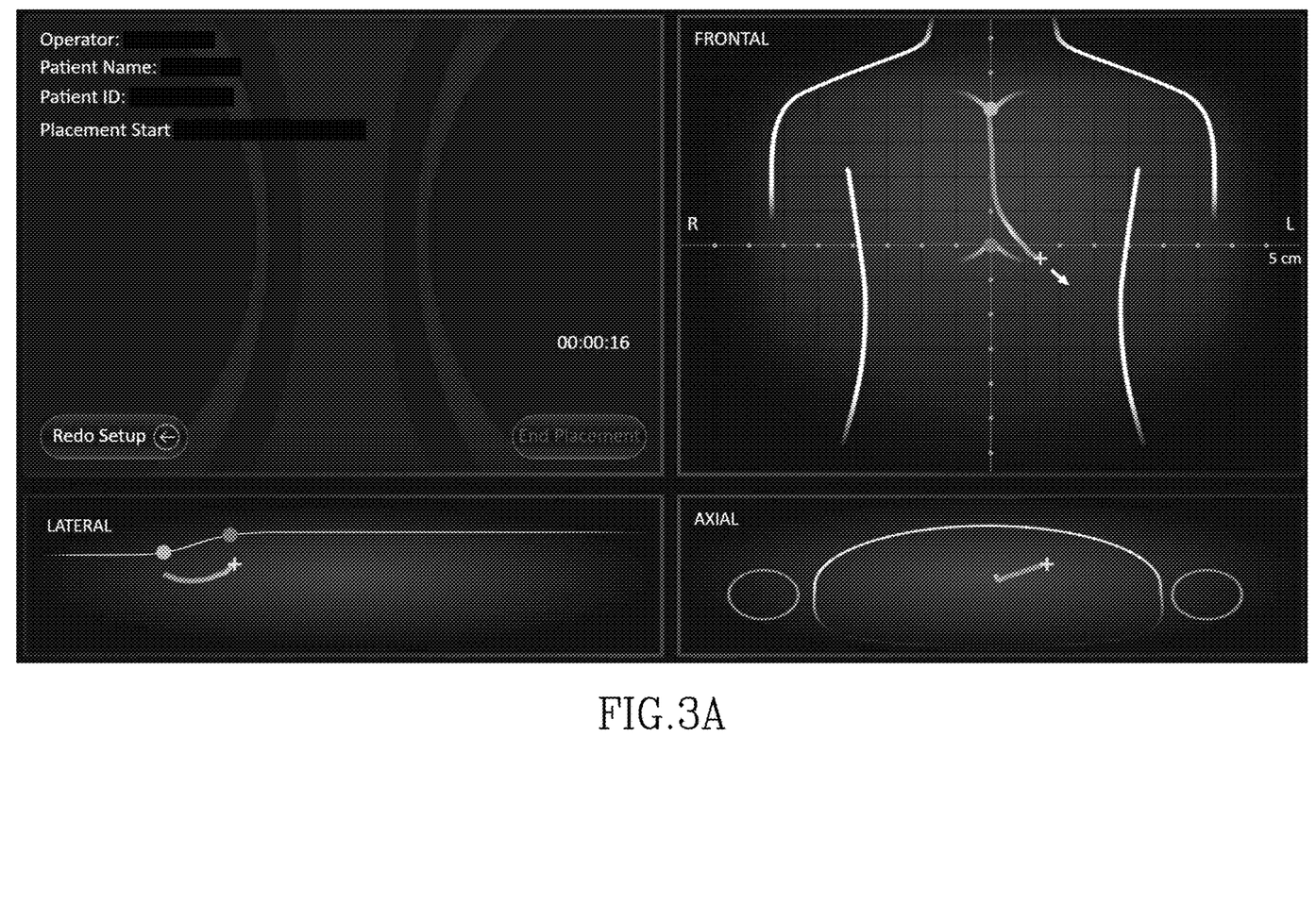
FIG. 3A shows a view of a "live" display of placement of an insertion device, in accordance with some embodiments.
Figure 3B:
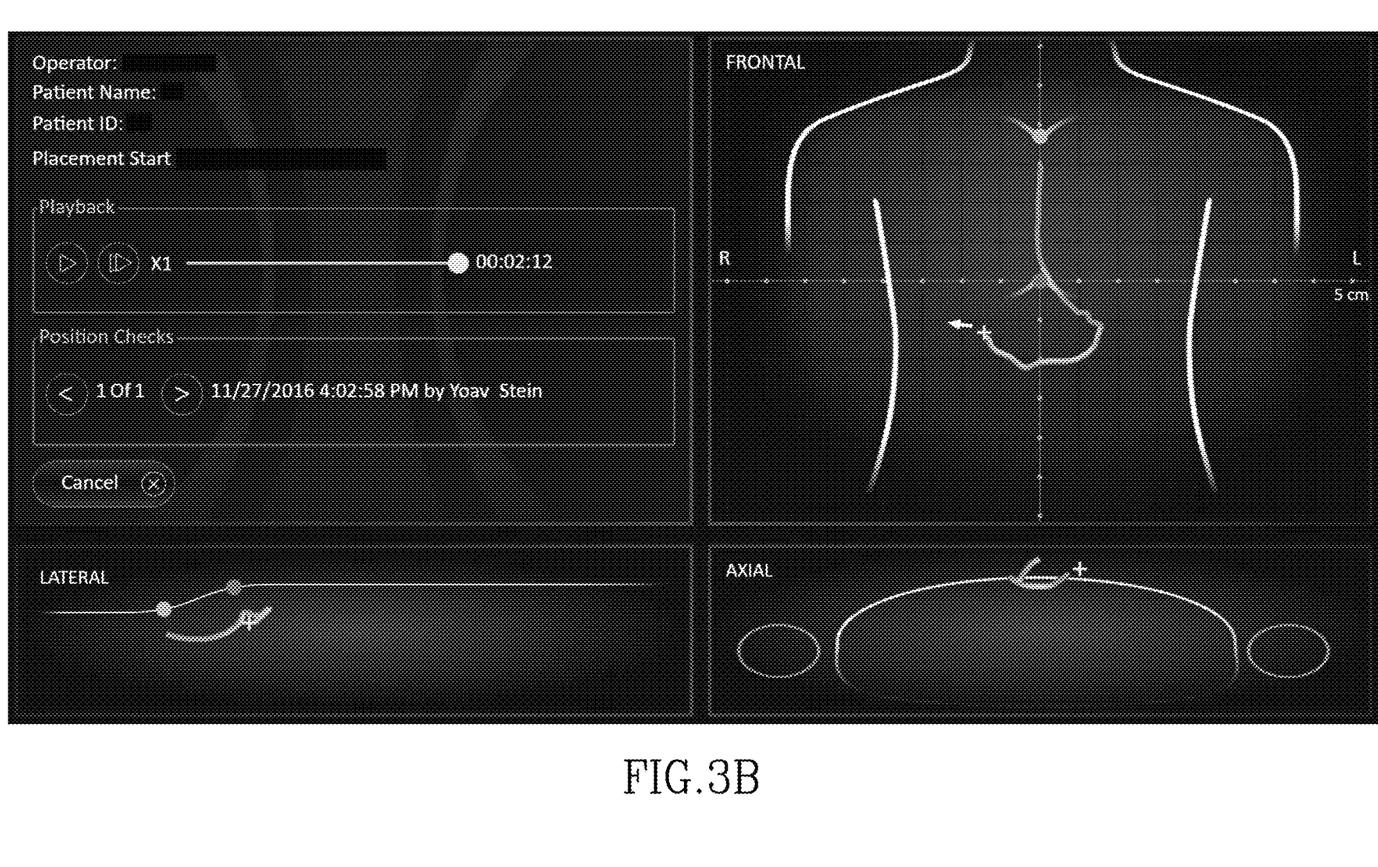
FIG. 3B shows a view of a "playback" display of placement of an insertion device, in accordance with some embodiments.

Reference is now made to FIG. 3A, which shows a view of a "live" display of placement of an insertion device, in accordance with some embodiments and to FIG. 3B, which shows a view of a "playback" display of placement of an insertion device, in accordance with some embodiments. Such displays may be presented on a monitor such as monitor 212. The left corner includes general information and patient's details, and in the display of FIG. 3B, also playback controls.

The tip's path is schematically drawn, enabling the caregiver to visualize the entire insertion path of the tube, until it reaches the desired location. Optionally, and as shown in FIGS. 3A and B, an arrow is near the tip of the path, indicating the actual direction to which the tube is pointing. Such arrow(s) may help the user to properly insert the tube (or better understand where and to which direction the tube is moving). The displays of both FIGS. 3A and B show three views of the patient's body: a frontal view shown at the top right side of the monitor, a lateral view shown at the bottom left side of the monitor, and an axial view shown at the bottom right side of the monitor. In some embodiments, different and/or additional views may be shown. The caregiver inserting the insertion medical device can view the indications on monitor 212 while manually maneuvering the medical implement into the patient's body, so as to guide it to the desired location in the body.

Figure 4:
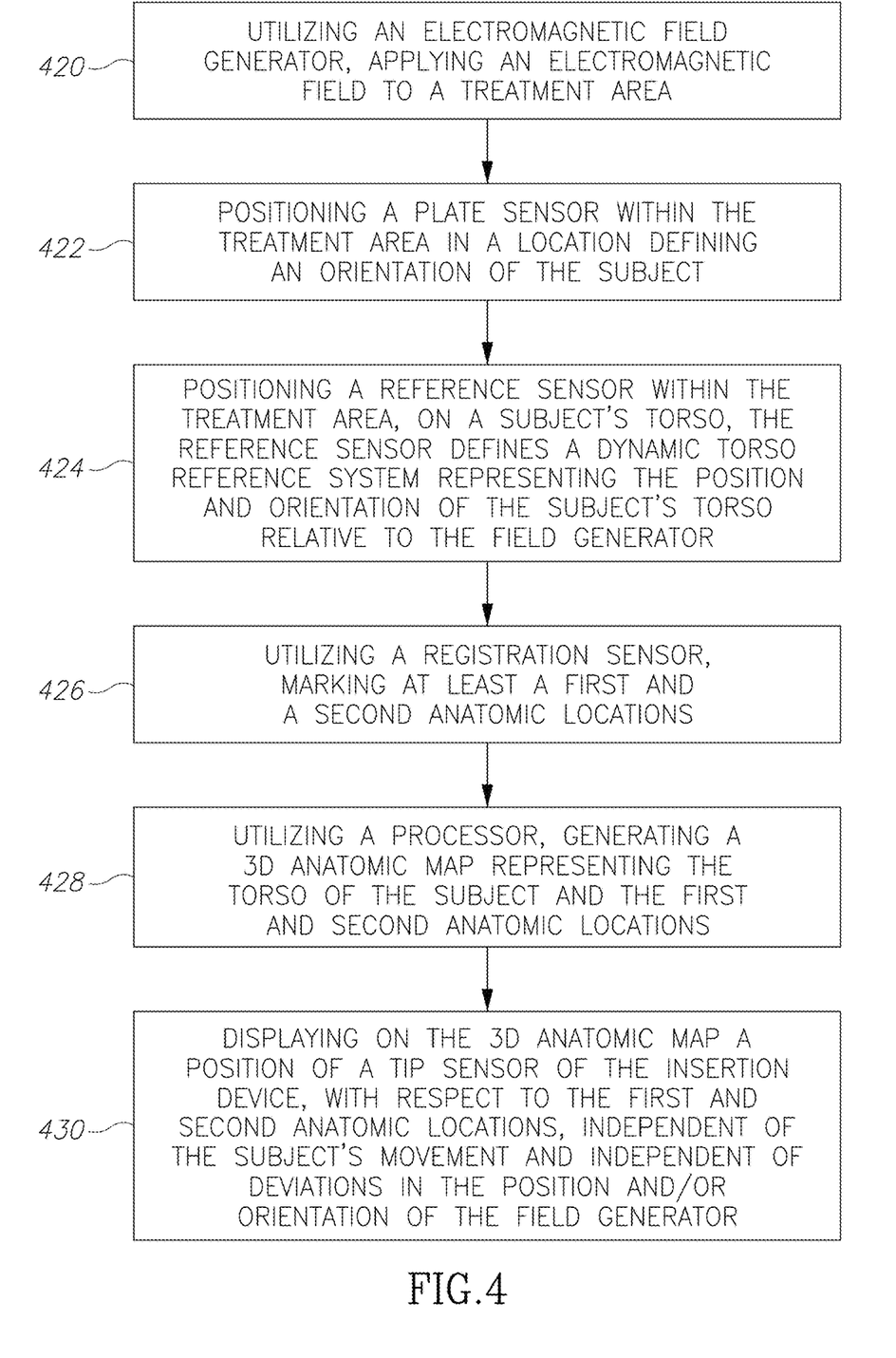
FIG. 4 is a flow chart of the steps of a method for guiding the position of an insertion medical device, in accordance with some embodiments.

Reference is now made to FIG. 4, which is a flow chart of the steps of a method for guiding the position of an insertion medical device, in accordance with some embodiments. Step 420 includes application of an electromagnetic field to a treatment area. Optionally, an electromagnetic field generator, such as electromagnetic field generator 202 of FIG. 2, is positioned such that the electromagnetic field covers the treatment area. A plate sensor, such as plate sensor 208 of FIGS. 2A-D, is positioned in a location defining an orientation of a subject (or at least the orientation of the body part that is being treated) (step 422). A reference sensor, such as reference sensor 204 of FIGS. 2A-D, is positioned on a patient within the treatment area, on a subject's torso, the reference sensor defines a reference coordinate system representing the position and orientation of the subject's torso relative to the field generator (step 424). Optionally, the reference sensor is positioned on a side of the patient's torso such as to indicate a body contour of the subject. At least a first and a second anatomic location are marked by utilizing a registration sensor (step 426). Optionally, a stylus sensor, such as stylus sensor 206 of FIGS. 2A-D, is manually operated to mark the at least first and second anatomic locations (e.g., 206a and 206b). Alternatively, one or more registration sensors are positioned over the at least first and second anatomic locations. Optionally, the first anatomic location is the suprasternal notch and the second anatomic location is the xiphoid process. Each of reference sensor 204, plate sensor 208, and the two marked anatomic locations 206a and 206b are present within the region of interest. Each of steps 420, 422 and 424, may be performed simultaneously or in an interchangeable order. An anatomic map representative of the subject's torso and the first and second anatomic locations is generated by utilizing a processor (step 428). The anatomic map may be generated based on signals received from reference sensor 204, plate sensor 208, and two marked anatomic locations 206a and 206b. A position and orientation of a tip sensor of the insertion device is displayed on the anatomic map, with respect to the first and second anatomic locations, independent of the subject's movement and independent of deviations in the position and/or orientation of the field generator (step 430). This can be accomplished when all sensors remain within the sensing volume of the field generator.

Optionally, the anatomic map shows a frontal upper view of the subject essentially parallel to the plate sensor, a side view of the subject essentially perpendicular to the plate sensor, an axial view of the subject. Optionally, the anatomic map enables visualization of the location of an insertion device (having an electromagnetic sensor configured to sense and/or interfere with the electromagnetic field generated by the field generator) within a subject's body by computing and displaying a position of the inserted device vis-à-vis first and second anatomic locations 206a and 206b. Optionally, the computing may include normalizing the position based at least on signals received from reference sensor 204 and plate sensor 208, and obtained continuously and/or in real-time during the procedure.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. Rather, the computer readable storage medium is a non-transient (i.e., not-volatile) medium.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A guidance system for positioning an enteral tube, comprising:
an electromagnetic field generator configured to be positioned externally to a subject's torso, said electromagnetic field generator configured to generate an electromagnetic field covering a treatment area on the subject's torso;
an enteral tube comprising a sensor assembly removably positioned within the enteral tube, the sensor assembly comprising an electromagnetic sensor at a distal tip thereof, said electromagnetic sensor configured to sense and/or interfere with the electromagnetic field generated by the field generator;
a reference sensor configured to be positioned, within the treatment area, on the subject's torso, the reference sensor configured to define a reference coordinate system representing the position and orientation of the subject's torso relative to the electromagnetic field, wherein the reference sensor is configured to be positioned independently of the insertion of the enteral tube;
a registration sensor configured to mark at least a first anatomic location relative to the reference coordinate system; and
a processing circuitry configured to:
operate said field generator, read signals obtained from said reference sensor and said registration sensor, and calculate a position and orientation of said reference sensor and said registration sensor relative to said field generator,
generate a 3D anatomic map representing the torso of the subject and the first anatomic location and a second anatomic location, and
visualize, on the 3D anatomic map, a position, orientation and/or path of the enteral tube with respect to the first and second anatomic locations, independent of the subject's movement and independent of deviations in the position and/or orientation of said field generator.

2. The system of claim 1, wherein said reference sensor is configured to be positioned on a side of the patient's torso, such that the 3D anatomic map further depicts a frontal body contour of the subject and wherein the registration sensor is further configured to mark a second anatomic location on the subject's torso.

3. The system of claim 1, wherein said reference sensor comprises two reference sensors positioned below the left and right claviculae respectfully, and wherein a distance between the first and second reference sensors is indicative of the width of the patient's torso.

4. The system of claim 1, wherein the 3D anatomic map shows a frontal upper view, a side view and an axial view of the subject's torso.

5. The system of claim 1, further comprising a monitor configured to display the 3D map.

6. The system of claim 1, wherein the registration sensor is a stylus configured to be manually operated.

7. The system of claim 1, wherein the first anatomic location is the suprasternal notch and the second anatomic location is the xiphoid process, and wherein a path display of the enteral tube relative to the first and second anatomic locations is indicative of a successful insertion.

8. The system of claim 1, wherein the enteral tube is a pediatric enteral tube.

9. The system of claim 1, wherein the enteral tube has outer diameter of 2 mm or less.

10. A method for guiding an insertion device, the method comprising:
utilizing an electromagnetic field generator to apply an electromagnetic field to a treatment area on the subject's torso;
positioning a reference sensor within the treatment area, on a subject's torso, the reference sensor defining a reference coordinate system representing the position and orientation of the subject's torso relative to the electromagnetic field;
marking at least a first locations using a registration sensor;
utilizing processing circuitry to:
operate said field generator,
read signals obtained from the reference sensor and the registration sensor, and calculate a position and orientation thereof relative to said field generator,
generate a 3D anatomic map representing the torso of the subject and the first anatomic location; and
displaying on the 3D anatomic map a position, orientation and/or path of a tip sensor of a sensor assembly removably positioned within the insertion device, with respect to the first and a second anatomic location, independent of the subject's movement and independent of deviations in the position and/or orientation of said field generator.

11. The method of claim 10, further comprising displaying a current location, orientation and/or path of the distal tip section of the insertion device on the 3D anatomic map and thus facilitate determination of a successful medical procedure.

12. The method of claim 10, wherein positioning the reference sensor comprises positioning thereof on a side of the patient's torso, such that the 3D anatomic map further depicts a body contour of the subject and wherein the method further comprises marking the second anatomic location utilizing the registration sensor.

13. The method of claim 10, wherein positioning the reference sensor comprises positioning two reference sensors below the left and right claviculae respectfully, wherein the method further comprises determining a width of the patient's torso based on a distance between the first and second reference sensors and calculating the position of the second anatomic location based on the width of the subject's torso and the left and right claviculae.

14. The method of claim 10, further comprising, once a desired position of the insertion device is reached, removing the sensor assembly from the insertion device.

15. The method of claim 10, wherein the 3D anatomic map shows a frontal upper view, a side view and an axial view of the subject.

16. The method of claim 10, wherein the registration sensor is a manually operated stylus.

17. The method of claim 10, wherein the insertion device is a pediatric enteral tube.

18. The method of claim 10, wherein the enteral tube has outer diameter of 2 mm or less.

19. The method of claim 10, wherein the first anatomic location is the suprasternal notch and the second anatomic location is the xiphoid process, and wherein a path display of the enteral tube relative to the first and second anatomic locations is indicative of a successful insertion.

* * * * *